US005837820A

United States Patent [19]
De Rose et al.

[11] Patent Number: 5,837,820
[45] Date of Patent: Nov. 17, 1998

[54] SEED SPECIFIC BIOTINYLATED PROTEIN, SBP65, FROM LEGUMINOUS PLANTS

[75] Inventors: Richard De Rose, Lyons; Roland Douce, Grenoble; Manuel Duval, Lyons; Claudette Job, Lyons; Dominique Job, Lyons, all of France

[73] Assignee: Rhone-Poulenc Agrochimie, Lyons, France

[21] Appl. No.: 346,429

[22] Filed: Nov. 29, 1994

[30] Foreign Application Priority Data

Nov. 29, 1993 [FR] France ................................... 93 14482
Feb. 14, 1994 [FR] France ................................... 94 01901

[51] Int. Cl.$^6$ ................................................. C07K 14/415
[52] U.S. Cl. .......................................... 530/370; 530/350
[58] Field of Search ....................................... 530/350, 370

[56] References Cited

PUBLICATIONS

Pyke et al. (1991) Plant Varieties and Seeds, 4(1), "Variation in Acetyl–CoA Carboxylase in Pea Varieties", pp. 23–30.
Bettey et al. (1992) J. Plant Physiol., 140, "Purification and Characterization of Acetyl–CoA Carboxylase from Developing Pea Embryos", pp. 513–520.
Nikolau et al. (1984a) Arch.Biochem.Biophys., 228(1), "Purification and Characterization of Maize Leaf Acetyl–Coenzyme A Carboxylase", pp. 86–94.
Nikolau et al. (1984b) Arch.Biochem.Biophys., 235(2), "Subcellular Distribution of Acetyl–Coenzyme A Carboxylase in Mesophyll Cells of Barley and Sorghum Leaves", pp. 555–561.
Hawke et al. (1990) Planta, 181(4), "Acetyl Coenzyme in Spices of *Triticym* of Different Ploidy", pp. 543–546.
Szmidzinski et al.(1994) Acta Biochimica Polonica, 41(2), "Molecular Cloning and Sequencing of the cDNA Encoding Plant 22 kDa Nuclease", pp. 139–140.
Duval et al. (1994a) *Biochem. J.*, 299 (1), "Developmental Patterns of Free and Protein–Bound Biotin During Maturation and Germination of Seeds of *Pisum sativum*: Characterization of a Novel Seed–Specific Biotinylated Protein", pp. 141–150.

Duval et al. (1994b) *Plant Mol. Biol.*, 26(1), "The Major Biotinyl Protein from *Pisum satvivum* Seeds Covalently Binds Biotin at a Novel Site", pp. 265–273.
Taniguchi et al.(1988) *Meiji Daigaku Nogakubu Kenkyu Hokoku*, 82, "Researches on Avidin–Like Compounds. II. Avidin–Like Proteins in Plant Seeds", pp. 1–14, in *Chem. Abstr.*, 111, Abstract No. 197088.
C. Alban et al. (1993) "Purification and Characterization of 3–Methylcrotonyl–Coenzyme A Carboxylase from Higher Plant Mitochondria" *Plant Physiol.* 102 957–965.
Y. Chen et al. (1993) "Purification and Characterization of 3–Methylcrotonyl–CoA Carboxylase from Somatic Embryos of Daucus Carota" *Archives of Biochem. and Biophys.* 305:1 103–109.
P. Gornicki et al. (1993) "Wheat Acetyl–Coa Carboxylase" *Plant Mol. Bio.* 22:3 547–552.
M. Duval et al. (1993) "Synthesis and Degradation of a Novel Biotinyl Protein in Development and Germinating Pea Seeds" *C.R. Acad. Sci. Paris, Sciences de la vie/Life Sciences* 316:12 1463–1470.
L. Dure III et al. (1989) "Common amino acid sequence domains among the LEA proteins of higher plants" *Plant Molecular Biology* 12: 475–486.
J.H. Choi et al. (1987) "Cloning of genes developmentally regulated during plant embryogenesis" *Proc. Nat'l Acad. Sci, USA* 84: 1906–1910.

*Primary Examiner*—Jon P. Weber
*Attorney, Agent, or Firm*—Scully, Scott, Murphy & Presser

[57] ABSTRACT

A biotinylated protein is disclosed which is obtained from the seeds of leguminous plants and which is expressed exclusively in the seeds and in no other tissue. The protein comprises at least one subunit of 50–85 kDa. Levels of the protein decrease rapidly as germination of the seed progresses. The protein does not exhibit the activity of either acetyl-CoA carboxylase or 3-methyl crotonyl-CoA carboxylase. In the pea, *Pisum sativum*, the protein is designated SBP65 and comprises 6–8 identical subunits, each having a molecular weight of about 65 kDa. The protein may be a useful marker for determining the germination stage of seeds.

5 Claims, 1 Drawing Sheet

SEED SPECIFIC BIOTINYLATED PROTEIN, SBP65, FROM LEGUMINOUS PLANTS

The present invention relates to a process for obtaining and to a new protein capable of being biotinylated in ripe seeds of plants belonging to leguminous, carrot and beet species and to its use as a molecular marker of the germination of these seeds.

BACKGROUND OF THE INVENTION

Germination is a complex development process for which there is currently available only a small amount of specific molecular data. This development programme, during which the cells of the embryo pass from a resting state to a state of intense metabolic activity, essentially begins during the imbibition phase. It ends, in the physiological sense, in the piercing of an organ of the nascent plantlet through the coats of the seed, Bewley et al. (1983).

The main techniques used to define the competence of seeds to germinate use conventional germination tests, that is to say that, for a given batch of seeds and under codified conditions (temperature, humidity, light, substrate), the percentage of germination at various times after sowing is measured. The criterion generally used to quantify the germination is the piercing of the coat of the seeds by an organ of the nascent plant. The majority of biochemical markers described to date are correlated with this phase. It therefore does not concern markers sensu stricto of germination but rather of the initial phases of growth (Fincher, 1989). For the moment, only a single example of an early marker is well documented. It relates to germine in cereals, a protein of the embryo, whose kinetics of appearance very closely follow the kinetics of imbibition (Lane et al., 1992). It should be noted that the initial imbibition phase is reversible up to a certain point. Following a controlled hydration of seeds, it is possible to dry them while retaining their biological integrity and their germinating ability. As soon as the plantlet appears, the commitment of the latter to its growth becomes irreversible. In fact, a dehydration at this stage irremediably leads to the death of the plantlets (Bewley & Black, 1983).

The pre-germination ("priming") processes developed by seed companies are based on the reversibility of the initial imbibition phase. The seeds are generally hydrated in a controlled way and are then dried (Karsen et al., 1989; Tarquis & Bradford, 1992). These processes contribute a true added value to the seeds because they:

1) make it possible to homogenize the batches of seeds with respect to germination, 2) make possible an appreciable saving in time for the emergence after sowing, since a certain number of biochemical processes necessary for accomplishing germination would already be carried out during priming, 3) make possible an improvement in the germinal quality of batches of aged seeds, probably due to the fact that mechanisms for repairing biological structures damaged during the final ripening of the seeds are deployed during the priming.

As markers of early stages of germination are not available, optimization of such processes rests solely on carrying out germination tests, which require several days of experimentation. Moreover, if the treatment fails (as batches of seeds are by nature heterogeneous, it is therefore necessary to optimize the treatment for each of the batches), the batch is lost. There therefore exists a significant need to find a molecular marker which is easy to detect and the possibility of continuously monitoring the imbibition phase, via such a molecular marker, would therefore constitute a considerable advance, making it possible to adapt the priming to each batch of seeds.

Plant cells are capable of synthesizing the main vitamins. One of them, biotin, acts as cofactor to a small number of enzymes, which play an essential role in cell metabolism, known under the name of biotin carboxylases (Knowles, 1989; Wurtele & Nikolau, 1990; Alban et al., 1993): acetyl-CoA carboxylase (EC 6.4.1.2), 3-methylcrotonyl-CoA carboxylase (EC 6.4.1.4), propionyl-CoA carboxylase (EC 6.4.1.3) and pyruvate carboxylase (EC 6.4.1.1). The study of these proteins is therefore of major importance in understanding the resurgence of metabolism during the germination of the seeds. Acetyl-CoA carboxylase is, in plants, the most studied of the biotin enzymes, because it constitutes the target of powerful herbicides in monocotyledon plants (Hoppe & Zacher, 1985; Burton et al., 1987a,b). This enzyme, in fact, plays a key role in the synthesis of fatty acids. The role of the other three biotin carboxylases in plants remains unknown for the moment. It is known that seeds containing lipid stores (Stumpf, 1980; Harwood, 1988), as well as pea seeds (Bettey et al., 1992), contain an acetyl-CoA carboxylase activity which is probably involved in the synthesis of storage triglycerides. On the other hand, it is not known if the seeds contain other biotinylated proteins and if they play a role during germination.

SUMMARY OF THE INVENTION

The subject of the present invention is therefore a pure protein of plant origin which is capable of being biotinylated, characterized in that it results from a seed of a species of crop plant and in that it comprises at least one unit of 50 to 85 kDa, is expressed in the seeds and in no other organ of the plant and disappears rapidly during the early phases of germination.

The subject of the present invention is more particularly a pure protein which is capable of being biotinylated and which results from the seed of leguminous species, for example pea, bean, lupin, lucerne, soya or lentil, but also in other species such as, for example, the umbelliferous species such as, for example, carrot or alternatively the Chenopodiaceae such as, for example, beet. In the case of pea, the protein is named SBP65. It also relates to the proteins equivalent to the latter which establish an interaction with biotin.

The invention also relates to new antibodies, characterized in that they recognize the protein SBP65.

It also relates to molecular probes, characterized in that they are derived from the protein SBP65 or from the equivalent proteins.

It also relates to the use of the specificity of tissue expression and of the pattern of development of these markers in order to measure as precisely as possible the state of progress of the germination, more particularly in the early imbibition phase, and in particular to their use as a protein and nucleic and molecular marker of germination in leguminous seeds, for example, pea, bean, lupin, lucerne, soya or lentil, but also in other species such as, for example, umbelliferous species such as, for example, carrot or alternatively the Chenopodiaceae such as, for example, beet. Detection of these markers can be carried out either by detection with specific antibodies, in the case of use in leguminous species, or directly using coloured visualization of biotin in the case of other crops such as carrot or beet.

This detection can be carried out using a device (kit), which also forms part of the invention.

Another subject of the invention is a process for the transformation of plant cells by DNA sequences encoding the protein SBP65 or an equivalent protein.

It likewise relates to a process for the transformation of plant cells by DNA sequences encoding an antisense RNA of the protein SBP65, or any equivalent biotinylated protein from the viewpoint of the pattern of development and the tissue expression, in order to inhibit the synthesis of such proteins and thus to create sterile plants.

A further subject of the invention is a process for the transformation of plants cells by DNA sequences expressing an RNA encoding a protein which could differ from SBP65 by its sequence and its method of interaction with biotin but whose construction would make it possible to provide for a specificity of tissue expression analogous to that of the protein SBP65 and the possibility of trapping, in the developing seeds, free biotin newly synthesized and/or absorbed from the soil by the plant with the aim of creating sterile plants.

The final subject of the invention is the plant cells transformed according to the above processes and the transformed plants obtained by regeneration of these transformed cells.

DETAILED DESCRIPTION OF THE INVENTION

Figure 1:
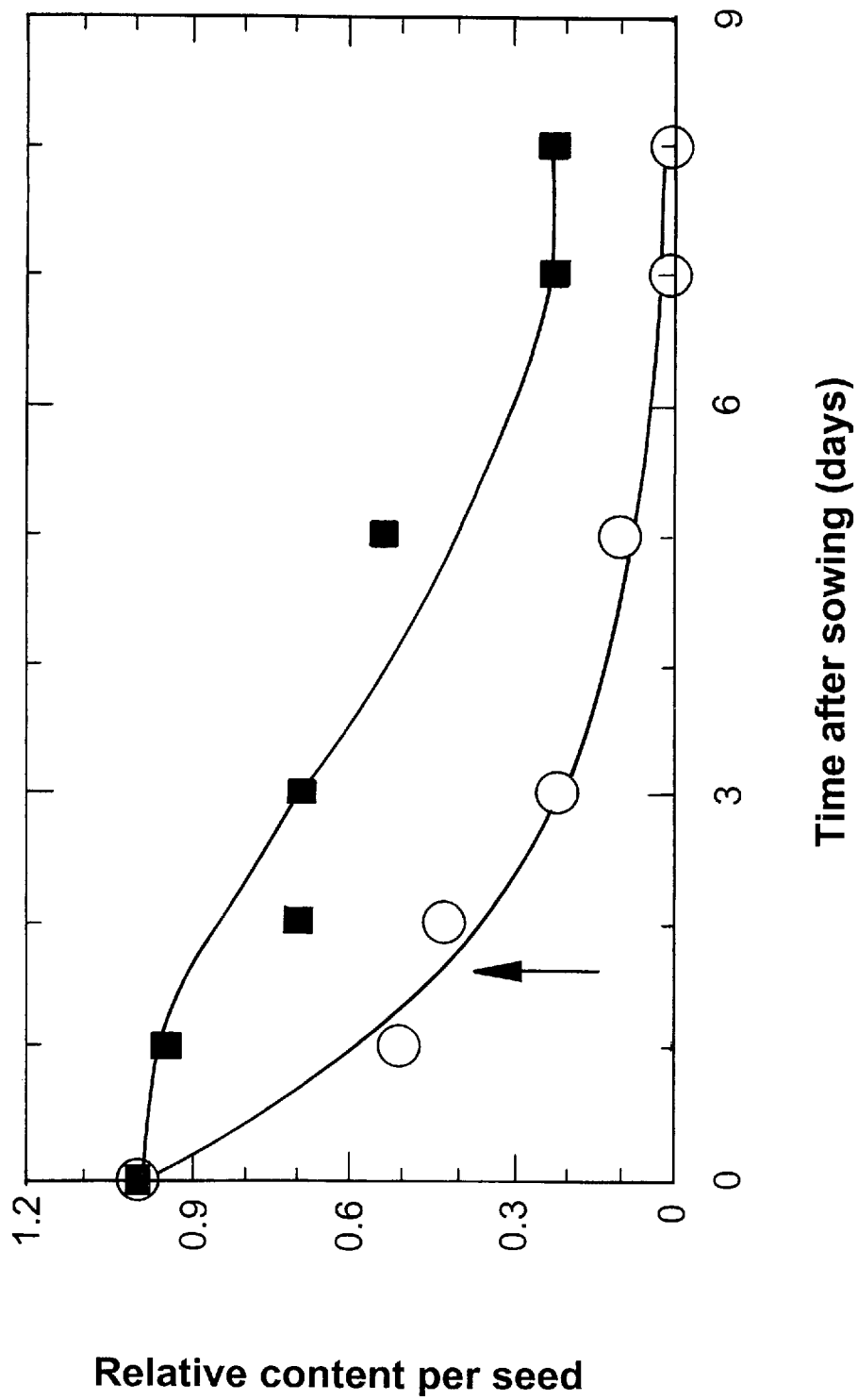
FIG. 1 graphically depicts levels of total proteins (■) versus levels of SBP65 protein (o) in peas seeds as germination progresses.

Characterization of proteins capable of being biotinylated:

Pea seed (pisum sativum cv. Douce Provence) is used as model. By virtue of the use of ELISA techniques and of specific marking with streptavidin [bacterial protein endowed with a very high specific affinity for biotin (Green, 1990)] coupled to peroxidase (Sigma), the biotinylated proteins are easily detectable in a total protein extract produced from a single seed. This quantification requires only a small number of stages which are easy to implement: grinding the seeds in a mixer of Waring blender type (30 sec), taking the powder up in a homogenization buffer (Hepes pH 8.0, containing various protease inhibitors; Alban et al., Plant Physiol. 102, 957–965, 1993), centrifuging (15 min at 20,000 g in Eppendorf-type centrifuging tubes) in order to remove the cell debris, and carrying out tests based on conventional ELISA techniques.

The proteins, which are capable of being biotinylated, of the crude extract can also be easily located, no longer as a mixture but individually, following the separation of the proteins of the total extract in a polyacrylamide gel in the presence of sodium dodecylsulfonate (SDS), electrotransfer of the proteins on a nitrocellulose membrane and specific visualization with streptavidin coupled to peroxidase (Nikolau et al., 1985; Alban et al., Plant Physiol. 102, 957–965, 1993). The latter technique has been optimized with the aim of making it possible to use equipment for the electrophoretic microanalysis of proteins in preformed polyacrylamide gels (PhastSystem and PhastTransfer of Pharmacia), which have the advantage of leading to a very rapid analysis of samples.

Using these methods, we have observed that ripe pea seeds contain a major protein capable of being biotinylated and which has a molecular weight of 65 kDa.

Measurements of enzymatic activity carried out as described by Alban et al. (1993) show that the crude extract contains two biotin carboxylase activities: acetyl-CoA carboxylase and 3-methylcrotonyl-CoA carboxylase. The propionyl-CoA carboxylase and pyruvate carboxylase activities are not detectable.

The protein SBP65 was purified to the state of homogeneity from a pea seed extract produced as described above and by using a chromatography technique on an affinity column consisting of avidin-Sepharose (Kohanski & Lane, 1990; Alban et al., 1993) [avidin is a chicken egg protein which, like bacterial streptavidin, is endowed with a very high specific affinity for biotin (Green, 1990)]. This method makes it possible to purify all the proteins capable of being biotinylated contained in the crude extract. In a subsequent stage, it is possible, by carrying out ion exchange chromatography on a Mono-Q HR 5/5 column (Pharmacia), to separate these proteins into two distinct fractions. One, not retained by the column, contains the pure protein SBP65. The other, retained by this column, is eluted in the presence of 0.3M KCl and contains the two main biotin carboxylase activities present in the crude extract: acetyl-CoA carboxylase and 3-methylcrotonyl-CoA carboxylase.

The main results of this purification are the following:

1) The protein SBP65 does not carry any of the biotin carboxylase activities (EC 6.4.1.1, EC 6.4.1.2, EC 6.4.1.3, and EC 6.4.1.4) described in micro-organisms, yeast and eukaryotes (Knowles, 1989). It contains one mole of biotin per mole of 65 kDa polypeptide, the binding of biotin to the protein being strong in nature, especially strong ionic or covalent in nature. Its molecular weight, estimated by gel filtration (Sephacryl S-300 HR, Pharmacia) is, in the native form, 450±60 kDa. This indicates that the native form of the protein SBP65 corresponds to the combination of six to eight identical subunits, each having a molecular weight of 65 kDa.

2) The acetyl-CoA carboxylase activity is carried by a biotinylated polypeptide of 200 kDa as described by Bettey et al. (1992).

3) The 3-methylcrotonyl-CoA carboxylase activity is carried by two polypeptides constituting the two subunits of the enzyme: one, biotinylated, of 75 kDa and the other, non-biotinylated, of 50 kDa, in agreement with the results of Alban et al. (1993) regarding the purification to the state of homogeneity of this enzyme from pea leaf.

SBP65 therefore corresponds to a new protein of plant origin capable of being biotinylated.

Tissue Distribution of the Protein

The purification to the state of homogeneity of the protein SBP65 has made it possible, by immunization of a rabbit, to obtain new specific antibodies which also form part of the invention. The use of these antibodies shows that the expression of the protein is specific to the seeds. It is not detected in any other organ of the plant (leaves, stems, roots, pods and flowers), whatever the state of development of the plant. Such tissue specificity is not found for the biotincarboxylases. The acetyl-CoA carboxylase and 3-methylcrotonyl-CoA carboxylase activities are, in fact, detectable in all organs of the plant.

Cloning of the cDNA Encoding the Protein

The anti-SBP65 antibodies were used to screen a cDNA bank corresponding to the polyadenylated mRNAs isolated from pea seeds. A recombinant bacterial clone (host:*Escherichia coli* K 12; cloning system: predigested lambda ZAP® II/Eco RI cloning kit, Stratagene), expressing a protein recognized by the anti-SBP65 antibodies, was isolated and the cDNA thus cloned was characterized. Its length is of the order of 2000 bases.

Sequencing experiments show that the cDNA contains, in the direction of the translation SEQ ID NOs: 5 and 7;

1) a consensus sequence for initiating the translation in plants: ATCAATGGC, (SEQ ID NO:1) is found at nucleotides 72–80 and 48–55 in SEQ ID NOs: 5 and 7 respectively.

2) a consensus signal for polyadenylation: AATAAA, (SEQ ID NO:2) is located at nucleotides 59–64 and 1829–1834 of SEQ ID NOs: 6 and 7 respectively.

3) a poly(A) tail consisting of 18 A residues (SEQ ID NO:2).

Moreover, the 5'-end of this cDNA contains sequence units corresponding exactly to those which we have determined by sequencing the protein from peptides obtained by cutting SBP65 with cyanogen bromide and trypsin. These sequence units correspond to 44 amino acid residues localized at the N-terminal end of SBP65 i.e., amino acid residues 17–27, 29–35, 37–49, and 62–74 of SEQ ID NOs: 5 and 7. Sequencing experiments of the protein SBP65 have additionally made it possible to identify the Lysine 103 as representing the amino acid residue carrying biotin.

SEQ ID NO:7 is the complete sequence of the cDNA encoding the protein according to the invention and which also forms part of the invention: its length is 1969 nucleotides. The region encoding the entire protein is 1653 nucleotides, from the nucleotide 51 to the nucleotide 1703. The sequence, from the nucleotide 47 to the nucleotide 55, corresponds to the consensus sequence found at the initiation codon of dicotyledon plants (AACAATGGC) SEQ ID NO:4. Nucloetides 1828 to 1838 correspond to the polyadenylation signal sequence. Sequence SEQ ID NO:7 also has the protein sequence translated from this cDNA, containing 551 residues. Peptide sequences obtained by microsequencing consist of amino acid residues 93–125 and amino acid residues 129–146 of SEQ ID NO:7. The Lysine residue in position 103 is that for binding biotin covalently (biocytin residue).

Comparison of the nucleotide and protein sequences obtained for the protein SBP65 with those contained in the Swiss-Prot and Gene Bank banks does not reveal any homology with a currently known protein. Presence of proteins equivalent to SBP65 in other seed species.

The use of anti-SBP65 antibodies shows that the protein is present in different varieties of pea seeds (Cador, Finale, Cash, Progreta, Twigy), and in different leguminous species (bean, soya, lentil, lupin, lucerne). For species not belonging to the leguminous family, the reactivity of the anti-SBP65 antibodies is low. However, in the case of carrot, two major biotinylated proteins of 62±2 kDa and 30±2 kDa are detected in ripe seeds, probably corresponding to the polypeptides revealed beforehand in the somatic embryo (Wurtele & Nikolau, 1992; Caffrey et al., 1993). These proteins disappear very rapidly during germination, before the appearance of the radicle is observed. The same type of results is obtained in the case of beet. Yet again a biotinylated protein of 62±2 kDa is easily recognizable in crude extracts of dry seeds, disappearing at a high rate during early phases of germination.

EXAMPLE 1

Development of the Total Proteins and of the Protein SBP65 During the Germination of Pea Seeds Germination experiments are carried out under glass, at 20° C., and under controlled light (photoperiod 12 h, white light in fluorescent tubes, 10–40 $\mu$E m$^{-2}$ s$^{-1}$). Ripe pea seeds (var. Douce Provence) are germinated on compost at zero-time; they are sprinkled each day with water. The seeds are withdrawn as a function of time. The arrow shows the piercing by the radicle. A crude extract is produced for each sample as indicated. FIG. 1 represents a curve showing the development, with time, of the relative content (1=100%) of the seeds in total proteins (■) [i.e. the storage proteins, the major proteins of the seeds (Bewley & Black, 1983)] and in protein SBP65 (○), the latter being specifically revealed by carrying out ELISA tests with anti-SBP65 antibodies. The results are displayed in standardized form with respect to the measurements carried out with the ripe seeds (zero-time). It may be observed that the protein SBP65 disappears very quickly during germination. A remarkable fact is that a considerable part of the initial content (of the order of 60%) disappears before the piercing by the radicle is observed (the latter is indicated by a vertical arrow). The kinetics of disappearance of SBP65 are thus much faster than those of the storage proteins of the seed. It is known that the mobilization of these stores begins when the radicle pierces the coats (Bewley et al., 1983). These results demonstrate that SBP65 is a marker of the early phases of germination.

EXAMPLE 2

To complement this study on the germination, the development in time of the expression of the protein SBP65 and of free biotin, that is to say the vitamin which is not complexed to proteins, during the ripening of the pea seeds is studied (by using the method described by Baldet et al., 1993). It is known that the plant cells have the enzymatic equipment necessary for the biosynthesis of this vitamin and that, moreover, the vitamin in its free form is found in the plant tissues such as the leaves in excess with respect to biotin bonded to proteins (Baldet et al., 1993). The main results obtained are the following:

1) In very young seeds, protein SBP65 is not yet present and free biotin is always in excess with respect to bonded biotin.

2) The maximum level of the protein SBP65 is detected in the final phase of ripening of the seeds, at the same time as the main storage substances, proteins, starch and triglycerides, accumulate and as the seeds enter into a dehydration phase. At this stage of development, bonded biotin (that is to say biotin mainly bonded to the protein SBP65, since the latter becomes, at this stage, the major biotinylated protein of the seeds) is in excess with respect to free biotin.

All these results show the biological role of the protein SBP65:

1) It constitutes a biotin store, used in germination for restarting the metabolism.

2) The protein SBP65 regulates the level of free biotin in the embryonic cell.

BIBLIOGRAPHIC REFERENCES

Alban, C., Baldet, P., Axiotis, S. & Douce, R. (1993), Plant Physiol., 102, 957–965

Baldet, P., Alban, C., Axiotis, S. & Douce, R. (1993), Arc. Biochem. Biophys., 303, 67–73

Bewley et al., (1983) in Physiology and Biochemistry of Seeds in Relation to Germination, Vol. 1, pp. 177–244, Springer-Verlag, Berlin Burton, J. D., Gronwald, J. W., Somers, D. A., Connelly, J. A., Gengenbach, B. G. & Wyse, D. L. (1987a), Biochem. Biophys. Res. Commun., 148, 1039–1044

Burton, J. D., Gronwald, J. W., Somers, D. A., Gengenbach, B. G. & Wyse, D. L. (1987b), Pestic. Biochem. Physiol., 34, 76–85

Caffrey, J. J., Keller, G., Wurtele, E. S. & Nikolau, B. J. (1993), Plant Physiol., 102, Abstract 524

Fincher, G. B. (1989), Annu. Rev. Plant Physiol. Plant Mol. Biol., 40, 305–346

Green, N. M. (1990), Methods Enzymol., 184, 51–67

Hoppe, H. H. & Zacher, H. (1985), Pestic. Biochem. Physiol., 24, 298–305

Karsen, C. M., Haigh, A., van der Toorn, P. & Weges, R. (1989), in Recent Advances in the Development and Germination of Seeds (Taylorson, R. B., ed.) NATO ASI series, Series A, Life sciences, Vol. 187, pp. 269–280

Knowles, J. R. (1989), Annu. Rev. Biochem. 58, 195–221

Kohanski, R. A. & Lane, M. D. (1990) Methods Enzymol., 184, 194–200

Lane, B. G., Cuming, A. C., Frégeau, J., Carpita, N. C., Hurkman, W. J., Bernier, F., Dratewa-Kos, E. & Kennedy, T. D. (1992), Eur. J. Biochem. 209, 961–969

Nikolau, B. J., Wurtele, E. S. & Stumpf, P. K. (1985), Anal. Biochem., 149, 448–453

Motel, A., Günther, S., Clauss, M., Kobek, K., Focke, M. & Lichtenthaler, H. K. (1993), Naturforsch., 48c, 294–3000

Shellhammer, J. & Meinke, D. (1990), Plant Physiol., 93, 1162–1167

Schneider, T., Dinkins, R., Robinson, K., Shellhammer, J. & Meinke, D. W. (1989), Dev. Biol., 131, 161–167

Tarquis, A. M. & Bradford, K. J. (1992), J. Exp. Bot., 43, 307–317

Wurtele, E. S. & Nikolau, B. J. (1990), Arch. Biochem. Biophys., 278, 179–186

Wurtele, E. S. & Nikolau, B. J. (1992), Plant Physiol., 99, 1699–1703

---

What is claimed is:

1. An isolated, biotinylated protein obtainable from the seed of a leguminous plant which comprises at least one subunit of about 50–85 kDa, wherein said subunit is expressed in the seed and in no other organ of the plant and wherein said subunit decreases rapidly as germination of said seed progresses.

2. The protein of claim 1 which binds antibodies to SBP65.

3. The protein of claim 2 wherein the leguminous plant is a pea and the protein comprises at least one subunit of about 65 kDa.

4. The protein of claim 3 which comprises the amino acid sequence encoded by at least one nucleic acid of SEQ ID NO:5 and SEQ ID NO:7.

5. The protein of claim 1 further comprising one mole of biotin per mole of 65 kDa polypeptide covalently bound thereto and having a molecular weight of 450±60 kDa corresponding to 6 to 8 subunits, each of said subunits having a molecular weight of 65 kDa and wherein said subunits do not exhibit acetyl-CoA carboxylase activity and 3-methyl crotonyl-CoA carboxylase activity.

* * * * *

UNITED STATES PATENT AND TRADEMARK OFFICE
CERTIFICATE OF CORRECTION

PATENT NO.    : 5,837,820
DATED         : Novrmber 17, 1998
INVENTOR(S) : Richard DeRose, et al.

It is certified that error appears in the above-identified patent and that said Letters Patent is hereby corrected as shown below:

On The Title Page, [56] References Cited, PUBLICATIONS:

"Characeterization" should read --Characterization--

Signed and Sealed this

Twentieth Day of March, 2001

Attest:

NICHOLAS P. GODICI

*Attesting Officer*                *Acting Director of the United States Patent and Trademark Office*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

A T C A A T G G C         9

( 2 ) INFORMATION FOR SEQ ID NO:2:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

A A T A A A         6

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

A A A A A A A A A   A A A A A A A A         1 8

( 2 ) INFORMATION FOR SEQ ID NO:4:

( i ) SEQUENCE CHARACTERISTICS:
        ( A ) LENGTH: 9 base pairs
        ( B ) TYPE: nucleic acid (C) STRANDEDNESS: double
(D) TOPOLOGY: linear (i i) MOLECULE TYPE: cDNA (x i) SEQUENCE DESCRIPTION: SEQ ID NO:4:

AACAATGGC                                                                                                                9

(2) INFORMATION FOR SEQ ID NO:5:

(i) SEQUENCE CHARACTERISTICS:
        (A) LENGTH: 530 base pairs
        (B) TYPE: nucleic acid
        (C) STRANDEDNESS: double
        (D) TOPOLOGY: linear (i i) MOLECULE TYPE: cDNA (i x) FEATURE:
        (A) NAME/KEY: CDS
        (B) LOCATION: 76..528

(x i) SEQUENCE DESCRIPTION: SEQ ID NO:5:

```
GAATTCGAGG  ATCCGGGTAC  CATGGTTTTT  TTTTTTTCA  TAACCAATAC  AGAGAAAAAC         60

GCACATCCAT  TATCA ATG GCA TCT GAA CAA TTA TCT CGC AGA GAA AAC ATC            111
                  Met Ala Ser Glu Gln Leu Ser Arg Arg Glu Asn Ile
                   1           5                      10

ACA ACC GAG AGA AAG ATT CAA AAC GCG GAA GAC AGT GTC CCT CAA AGG              159
Thr Thr Glu Arg Lys Ile Gln Asn Ala Glu Asp Ser Val Pro Gln Arg
         15                  20                  25

ACA ACC CAC TTC GAG CTT AGA GAG ACC CAC GAA CTT GGA CCA AAC TTT              207
Thr Thr His Phe Glu Leu Arg Glu Thr His Glu Leu Gly Pro Asn Phe
         30                  35                  40

CAG TCT CTC CCT CGC AAC GAG AAT CAA GCT TAC CTT GAC CGT GGT GCA              255
Gln Ser Leu Pro Arg Asn Glu Asn Gln Ala Tyr Leu Asp Arg Gly Ala
45                   50                  55                  60

CGT GCT CCT TTG AGT GCA AAT GTA TCA GAA AGT TAC CTT GAT CGT GCA              303
Arg Ala Pro Leu Ser Ala Asn Val Ser Glu Ser Tyr Leu Asp Arg Ala
                 65                  70                  75

CGT GTT CCT TTG AAT GCA AAT ATA CCA GAA CAC AGA GTT AGA GAA AAA              351
Arg Val Pro Leu Asn Ala Asn Ile Pro Glu His Arg Val Arg Glu Lys
             80                  85                  90

GAA GAT TTT GGT GGT GTT CGT GAT ATG GGA AAG TTT CAG ATG GAA TCG              399
Glu Asp Phe Gly Gly Val Arg Asp Met Gly Lys Phe Gln Met Glu Ser
         95                  100                 105

AAA GGA GGG AAT AAG AGT TTG GCC GAA GAT AGA GAA ACT CTC GAT ACA              447
Lys Gly Gly Asn Lys Ser Leu Ala Glu Asp Arg Glu Thr Leu Asp Thr
    110                 115                 120

CGA TCT AGA ATG GTT ACT GGA ACA CCT CAC ATT AAA GAA GCA TCG GGA              495
Arg Ser Arg Met Val Thr Gly Thr Pro His Ile Lys Glu Ala Ser Gly
125             130                 135                 140

AAA GGA CAA GTT GTG GAG GAA AGA GAG AGA GCG AG                               530
Lys Gly Gln Val Val Glu Glu Arg Glu Arg Ala
                145                 150
```

(2) INFORMATION FOR SEQ ID NO:6:

(i) SEQUENCE CHARACTERISTICS:
        (A) LENGTH: 925 base pairs
        (B) TYPE: nucleic acid
        (C) STRANDEDNESS: double
        (D) TOPOLOGY: linear (i i) MOLECULE TYPE: cDNA (x i) SEQUENCE DESCRIPTION: SEQ ID NO:6:

```
GTCGACAGTG  GATGGAACTA  GGGCTGCTGC  GAATGCTGTT  GAAGGAGCGG  TTGGGTATGT      60

TGCACTTAAA  GCTTCTGAGC  TTGCGGCGAA  ATCGGTGGAA  ACTGTTAAGG  GTTTGGCTGC     120

TTCTGCTGGT  GAAACTGCTA  AGGAGTTTAC  TGCTAGGAAG  AAAGAAGAAT  CATGGCGGGA     180

ATATGAGGCT  AAAAGGGCTT  CTCAACTTCA  GGAAGGTGAA  GAAATCTTGC  CATCTACCGG     240

AGGTATCGGA  AAAGTGTTAC  CCAGTGGAGA  AGAACTCAA   GCACAAGGAA  CCAATCTTCA     300

AGAGAAGGTA  CAAGGAAAAG  GAAGTGATAT  ATTAGGAGCT  GTGACTGAAA  CTGTGAGTGA     360

CATTGGAAGT  AGCATGATTA  AACCAATAGA  TAATGCTAAT  ACTAAAGTTA  AGGAACATGG     420

TGGCACTACT  ATTACACCAA  AGGACAAGA   TGCTGGTGGT  GTTTTGGATG  CTATTGGTGA     480

AACTATAGCT  GAGATTGCAC  ATACAACTAA  AGTCATTGTT  GTTGGTGAAG  ATGATGAAGT     540

AGAAAAGTCA  ATGCAGAAGA  ATATTGGGTC  AGATTCTCAC  TCTCTTGATC  GTGCCAAGCA     600

TGAAGGATAT  AGAGCACCAA  AGAATAATGT  TTCTTAATTC  CAAAGTTTGA  AGACAATGAA     660

TGTGTTTGTT  TGATGCAGAA  GTTTAGTAAT  ATGTTAATCT  TAATTAGCTG  TCAGTGAAGA     720

AGTTCAATGT  TTTGTGGCTT  TGTTTTATGG  AGTTGTGTGA  ATAAATTACA  ATCTCATTCT     780

TGAGATTGTC  AATAATAGCA  AATATATCTT  ATGCTTATGT  CTTTTGTAAG  TCAATGTTGT     840

AATGTAATAA  TATATACTTT  TATTTAATAT  TCTGTTATTG  CTAAAAAAAA  AAAAAAAAAA     900

CCATGGTACC  CGGATCCTCG  AATTC                                              925
```

( 2 ) INFORMATION FOR SEQ ID NO:7:

( i ) SEQUENCE CHARACTERISTICS:
        ( A ) LENGTH: 1969 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 51..1703

( x i ) SEQUENCE DESCRIPTION: SEQ ID NO:7:

```
TTTTTTTTTT  TTTCATAACC  AATACAGAGA  AAAACGCACA  TCCATTATCA  ATG GCA         56
                                                             Met Ala
                                                               1

TCT GAA CAA TTA TCT CGC AGA GAA AAC ATC ACA ACC GAG AGA AAG ATT           104
Ser Glu Gln Leu Ser Arg Arg Glu Asn Ile Thr Thr Glu Arg Lys Ile
         5              10                  15

CAA AAC GCG GAA GAC AGT GTC CCT CAA AGG ACA ACC CAC TTC GAG CTT           152
Gln Asn Ala Glu Asp Ser Val Pro Gln Arg Thr Thr His Phe Glu Leu
     20              25                  30

AGA GAG ACC CAC GAA CTT GGA CCA AAC TTT CAG TCT CTC CCT CGC AAC           200
Arg Glu Thr His Glu Leu Gly Pro Asn Phe Gln Ser Leu Pro Arg Asn
 35              40                  45                  50

GAG AAT CAA GCT TAC CTT GAC CGT GGT GCA CGT GCT CCT TTG AGT GCA           248
Glu Asn Gln Ala Tyr Leu Asp Arg Gly Ala Arg Ala Pro Leu Ser Ala
                 55                  60                  65

AAT GTA TCA GAA AGT TAC CTT GAT CGT GCA CGT GTT CCT TTG AAT GCA           296
Asn Val Ser Glu Ser Tyr Leu Asp Arg Ala Arg Val Pro Leu Asn Ala
             70                  75                  80

AAT ATA CCA GAA CAC AGA GTT AGA GAA AAA GAA GAT TTT GGT GGT GTT           344
Asn Ile Pro Glu His Arg Val Arg Glu Lys Glu Asp Phe Gly Gly Val
         85                  90                  95

CGT GAT ATG GGA AAG TTT CAG ATG GAA TCG AAA GGA GGG AAT AAG AGT           392
Arg Asp Met Gly Lys Phe Gln Met Glu Ser Lys Gly Gly Asn Lys Ser
```

-continued

```
                       100                          105                             110
TTG  GCC  GAA  GAT  AGA  GAA  ACT  CTC  GAT  ACA  CGA  TCT  AGA  ATG  GTT  ACT      440
Leu  Ala  Glu  Asp  Arg  Glu  Thr  Leu  Asp  Thr  Arg  Ser  Arg  Met  Val  Thr
115            120                      125                           130

GGA  ACA  CCT  CAC  ATT  AAA  GAA  GCA  TCG  GAA  AAA  GGA  CAA  GTT  GTG  GAG      488
Gly  Thr  Pro  His  Ile  Lys  Glu  Ala  Ser  Gly  Lys  Gly  Gln  Val  Val  Glu
                    135                      140                           145

GAA  AGA  GAG  AGA  GCG  AGA  GAA  AGA  GCA  ATG  GAA  GAA  GAG  AAA  AGG          536
Glu  Arg  Glu  Arg  Ala  Arg  Glu  Arg  Ala  Met  Glu  Glu  Glu  Lys  Arg
               150                      155                      160

TTA  ACA  ATG  GAA  GAG  ATA  TCG  AAG  TAT  AGA  AAC  CAA  GCT  CAA  CAA  AGT      584
Leu  Thr  Met  Glu  Glu  Ile  Ser  Lys  Tyr  Arg  Asn  Gln  Ala  Gln  Gln  Ser
               165                      170                      175

GCA  TTG  GAA  GCG  CTT  TCA  GCA  GCA  CAA  GAG  AAA  TAC  GAA  AGA  GCG  AAA      632
Ala  Leu  Glu  Ala  Leu  Ser  Ala  Ala  Gln  Glu  Lys  Tyr  Glu  Arg  Ala  Lys
          180                      185                      190

CAA  GCA  ACA  AAT  GAA  ACA  CTA  CGC  AAC  ACG  ACA  CAG  GCT  GCA  CAA  GAG      680
Gln  Ala  Thr  Asn  Glu  Thr  Leu  Arg  Asn  Thr  Thr  Gln  Ala  Ala  Gln  Glu
195                      200                      205                      210

AAA  GGA  GAA  GCA  GCA  CAA  GCG  AAA  GAT  GCA  ACT  TTT  GAG  AAA  ACA  CAA      728
Lys  Gly  Glu  Ala  Ala  Gln  Ala  Lys  Asp  Ala  Thr  Phe  Glu  Lys  Thr  Gln
                    215                      220                      225

CAA  GGT  TAT  GAA  ATG  ACA  GGA  GAC  ACA  GTT  TCA  AAT  TCT  GCA  AGA  ACT      776
Gln  Gly  Tyr  Glu  Met  Thr  Gly  Asp  Thr  Val  Ser  Asn  Ser  Ala  Arg  Thr
               230                      235                      240

GCT  TCT  GAG  AAA  GCA  GCA  CAG  GCT  AAA  AAT  ACA  ACT  CTT  GGA  AAG  ACA      824
Ala  Ser  Glu  Lys  Ala  Ala  Gln  Ala  Lys  Asn  Thr  Thr  Leu  Gly  Lys  Thr
          245                      250                      255

CAA  CAA  GGT  TAT  GAG  GCA  ACA  AGA  GAC  ACA  GTT  TCA  AAT  GCT  GCA  AGA      872
Gln  Gln  Gly  Tyr  Glu  Ala  Thr  Arg  Asp  Thr  Val  Ser  Asn  Ala  Ala  Arg
260                      265                      270

ACT  GCG  GCG  GAG  TAT  GCT  ACT  CCT  GCT  GCG  GAG  AAA  GCC  AGG  TGT  GTG      920
Thr  Ala  Ala  Glu  Tyr  Ala  Thr  Pro  Ala  Ala  Glu  Lys  Ala  Arg  Cys  Val
275                      280                      285                      290

GCT  GTT  CAG  GCG  AAA  GAT  GTT  ACT  CTG  GAA  ACA  GGT  AAG  ACA  GCG  GCG      968
Ala  Val  Gln  Ala  Lys  Asp  Val  Thr  Leu  Glu  Thr  Gly  Lys  Thr  Ala  Ala
               295                      300                      305

GAG  AAA  GCC  AAG  TGT  GCC  GCG  GAA  ATT  GCT  GCC  AAA  GTG  GCG  GTT  GAT     1016
Glu  Lys  Ala  Lys  Cys  Ala  Ala  Glu  Ile  Ala  Ala  Lys  Val  Ala  Val  Asp
               310                      315                      320

TTG  AAG  GAG  AAG  GCC  ACT  GTG  GCA  GGG  TGG  ACT  GCG  TCG  CAT  TAT  GCC     1064
Leu  Lys  Glu  Lys  Ala  Thr  Val  Ala  Gly  Trp  Thr  Ala  Ser  His  Tyr  Ala
          325                      330                      335

ACA  CAG  TTG  ACA  GTG  GAT  GGA  ACT  AGG  GCT  GCT  GCG  AAT  GCT  GTT  GAA     1112
Thr  Gln  Leu  Thr  Val  Asp  Gly  Thr  Arg  Ala  Ala  Ala  Asn  Ala  Val  Glu
340                      345                      350

GGA  GCG  GTT  GGG  TAT  GTT  GCA  CCT  AAA  GCT  TCT  GAG  CTT  GCG  GCG  AAA     1160
Gly  Ala  Val  Gly  Tyr  Val  Ala  Pro  Lys  Ala  Ser  Glu  Leu  Ala  Ala  Lys
355                      360                      365                      370

TCG  GTG  GAA  ACT  GTT  AAG  GGT  TTG  GCT  GCT  TCT  GCT  GGT  GAA  ACT  GCT     1208
Ser  Val  Glu  Thr  Val  Lys  Gly  Leu  Ala  Ala  Ser  Ala  Gly  Glu  Thr  Ala
                    375                      380                      385

AAG  GAG  TTT  ACT  GCT  AGG  AAG  AAA  GAA  GAA  TCA  TGG  CGG  GAA  TAT  GAG     1256
Lys  Glu  Phe  Thr  Ala  Arg  Lys  Lys  Glu  Glu  Ser  Trp  Arg  Glu  Tyr  Glu
               390                      395                      400

GCT  AAA  AGG  GCT  TCT  CAA  CTT  CAG  GAA  GGT  GAA  GAA  ATC  TTG  CCA  TCT     1304
Ala  Lys  Arg  Ala  Ser  Gln  Leu  Gln  Glu  Gly  Glu  Glu  Ile  Leu  Pro  Ser
               405                      410                      415

ACC  GGA  GGT  ATC  GGA  AAA  GTG  TTA  CCC  AGT  GGA  GAA  AGA  ACT  CAA  GCA     1352
Thr  Gly  Gly  Ile  Gly  Lys  Val  Leu  Pro  Ser  Gly  Glu  Arg  Thr  Gln  Ala
```

-continued

| | | | | 420 | | | | | 425 | | | | | 430 | | |
|---|---|---|---|---|---|---|---|---|---|---|---|---|---|---|---|---|
| CAA | GGA | ACC | AAT | CTT | CAA | GAG | AAG | GTA | CAA | GGA | AAA | GGA | AGT | GAT | ATA | 1400 |
| Gln | Gly | Thr | Asn | Leu | Gln | Glu | Lys | Val | Gln | Gly | Lys | Gly | Ser | Asp | Ile | |
| 435 | | | | | 440 | | | | | 445 | | | | | 450 | |
| TTA | GGA | GCT | GTG | ACT | GAA | ACT | GTG | AGT | GAC | ATT | GGA | AGT | AGC | ATG | ATT | 1448 |
| Leu | Gly | Ala | Val | Thr | Glu | Thr | Val | Ser | Asp | Ile | Gly | Ser | Ser | Met | Ile | |
| | | | | 455 | | | | | 460 | | | | | 465 | | |
| AAA | CCA | ATA | GAT | AAT | GCT | AAT | ACT | AAA | GTT | AAG | GAA | CAT | GGT | GGC | ACT | 1496 |
| Lys | Pro | Ile | Asp | Asn | Ala | Asn | Thr | Lys | Val | Lys | Glu | His | Gly | Gly | Thr | |
| | | | 470 | | | | | 475 | | | | | 480 | | | |
| ACT | ATT | ACA | CCA | AAA | GGA | CAA | GAT | GCT | GGT | GGT | GTT | TTG | GAT | GCT | ATT | 1544 |
| Thr | Ile | Thr | Pro | Lys | Gly | Gln | Asp | Ala | Gly | Gly | Val | Leu | Asp | Ala | Ile | |
| | | 485 | | | | | 490 | | | | | 495 | | | | |
| GGT | GAA | ACT | ATA | GCT | GAG | ATT | GCA | CAT | ACA | ACT | AAA | GTC | ATT | GTT | GTT | 1592 |
| Gly | Glu | Thr | Ile | Ala | Glu | Ile | Ala | His | Thr | Thr | Lys | Val | Ile | Val | Val | |
| | 500 | | | | | 505 | | | | | 510 | | | | | |
| GGT | GAA | GAT | GAT | GAA | GTA | GAA | AAG | TCA | ATG | CAG | AAG | AAT | ATT | GGG | TCA | 1640 |
| Gly | Glu | Asp | Asp | Glu | Val | Glu | Lys | Ser | Met | Gln | Lys | Asn | Ile | Gly | Ser | |
| 515 | | | | | 520 | | | | | 525 | | | | | 530 | |
| GAT | TCT | CAC | TCT | CTT | GAT | CGT | GCC | AAG | CAT | GAA | GGA | TAT | AGA | GCA | CCA | 1688 |
| Asp | Ser | His | Ser | Leu | Asp | Arg | Ala | Lys | His | Glu | Gly | Tyr | Arg | Ala | Pro | |
| | | | | 535 | | | | | 540 | | | | | 545 | | |
| AAG | AAT | AAT | GTT | TCT | TAATTCCAAA | | GTTGAAGAC | | AATGAATGTG | | TTTGTTTGAT | | | | | 1743 |
| Lys | Asn | Asn | Val | Ser | | | | | | | | | | | | |
| | | | | 550 | | | | | | | | | | | | |
| GCAGAAGTTT | | AGTAATATGT | | TAATCTTAAT | | TAGCTGTCAG | | TGAAGAAGTT | | CAATGTTTTG | | | | | | 1803 |
| TGGCTTTGTT | | TTATGGAGTT | | GTGTGAATAA | | ATTACAATCT | | CATTCTTGAG | | ATTGTCAATA | | | | | | 1863 |
| ATAGCAAATA | | TATCTTATGC | | TTATGTCTTT | | TGTAAGTCAA | | TGTTGTAATG | | TAATAATATA | | | | | | 1923 |
| TACTTTTATT | | TAATATTCTG | | TTATTGCTAA | | AAAAAAAAAA | | AAAAAA | | | | | | | | 1969 |